United States Patent [19]

Williams et al.

[11] Patent Number: 5,171,989
[45] Date of Patent: Dec. 15, 1992

[54] METHOD AND APPARATUS FOR CONTINUOUS SAMPLE ICE MATRIX PRODUCTION FOR LASER DESORPTION IN MASS SPECTROMETRY

[75] Inventors: Evan R. Williams, Palo Alto; Glenn C. Jones; Richard N. Zare, both of Stanford, all of Calif.

[73] Assignee: Board of Trustees of Leland Stanford Jr. University, Stanford, Calif.

[21] Appl. No.: 826,924

[22] Filed: Jan. 24, 1992

[51] Int. Cl.$^5$ .............................................. H01J 49/04
[52] U.S. Cl. ...................................... 250/288; 422/81; 73/863.11; 73/864.81
[58] Field of Search ............. 250/288, 288 A; 422/81; 73/863.11, 864.81

[56] References Cited

U.S. PATENT DOCUMENTS 4,920,264  4/1990  Becker ................................ 250/282
4,988,879  1/1991  Zare et al. ...................... 250/423 P

OTHER PUBLICATIONS

Karas et al., "Ultraviolet-Laser Desorption/Ionization Mass Spectrometry of Femtomolar Amounts of Large Proteins," *Biomed. & Envir. Mass Spec.*, 18, 841–843 (1989).
Overberg et al., "Matrix-Assisted Infrared-Laser (2.94 μm) Desorption/Ionization Mass Spectrometry of Large Biomolecules," *Rapid Comm. in Mass Spectro.*, 4:8 293–296 (1990).
Beavis et al., "Factors Affecting the Ultraviolet Laser Desorption of Proteins", *Rapid Comm. in Mass Spectro.*, 3:7, 233–237 (1989).
Nelson et al., "Time-of-Flight Mass Spectrometry of Nucleic Acids by Laser Ablation and Ionization from a Frozen Aqueous Matrix," *Rapid Comm. in Mass Spectro.*, 4:9, 348–351 (1990).
Nelson et al., "Volatilization of High Molecular Weight DNA by Pulsed Laser Ablation of Frozen Aqueous Solutions," *Science*, 246, 1585–1587 (1989).
Tsuda et al., "Device to Transform the Liquid Chromatographic Effluent to a Continuous Solid Plug: A New Approach to Direct Liquid Introduction for Liquid Chromatography-Mass Spectrometry," *J. of Chrom.*, 456, 363–369 (1988).
Huang et al., "Use of an On-Columnh Frit in Capillary Zone Electrophoresis: Sample Collection," *Anal. Chem.*, 62, 443–446 (1990).

*Primary Examiner*—Jack I. Berman
*Attorney, Agent, or Firm*—Majestic, Parsons, Siebert & Hsue

[57] ABSTRACT

A method and apparatus for continuously introducing samples for mass spectrometry analysis which comprises providing sample molecules in an aqueous solution containing one or more organic solvents, preferably ethylene glycol, introducing said aqueous solution into the vacuum chamber of an ion source to enable said solution to solidify into a thread of solid matrix, and exposing the solid matrix to a source of energy to desorb sample molecules to be analyzed. The desorbed molecules are then photoionized and focused into a mass spectral analysis zone. The technique is suitable for interfacing liquid chromatographic separation techniques.

30 Claims, 4 Drawing Sheets

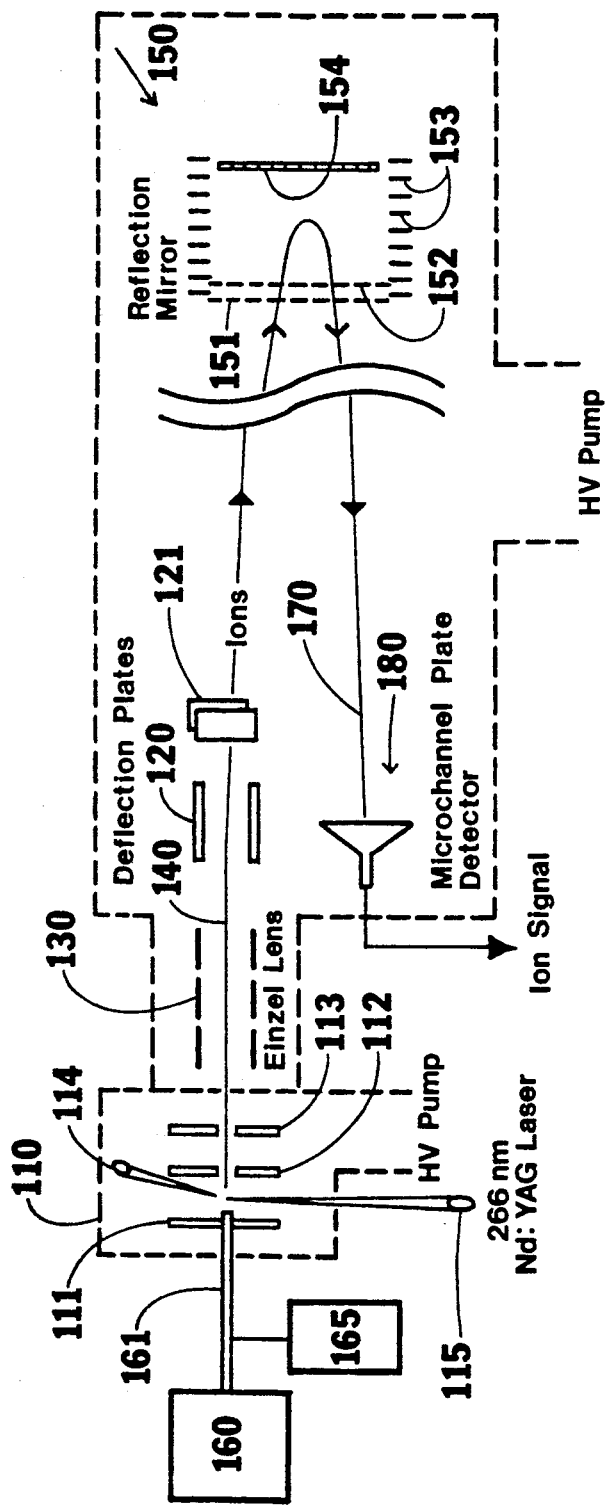
Fig. —1.
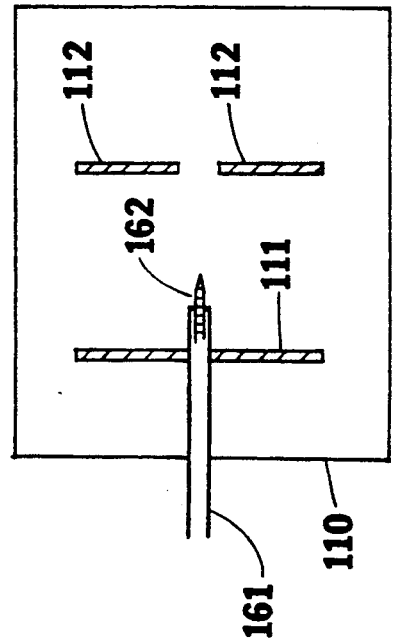
Fig. —2.

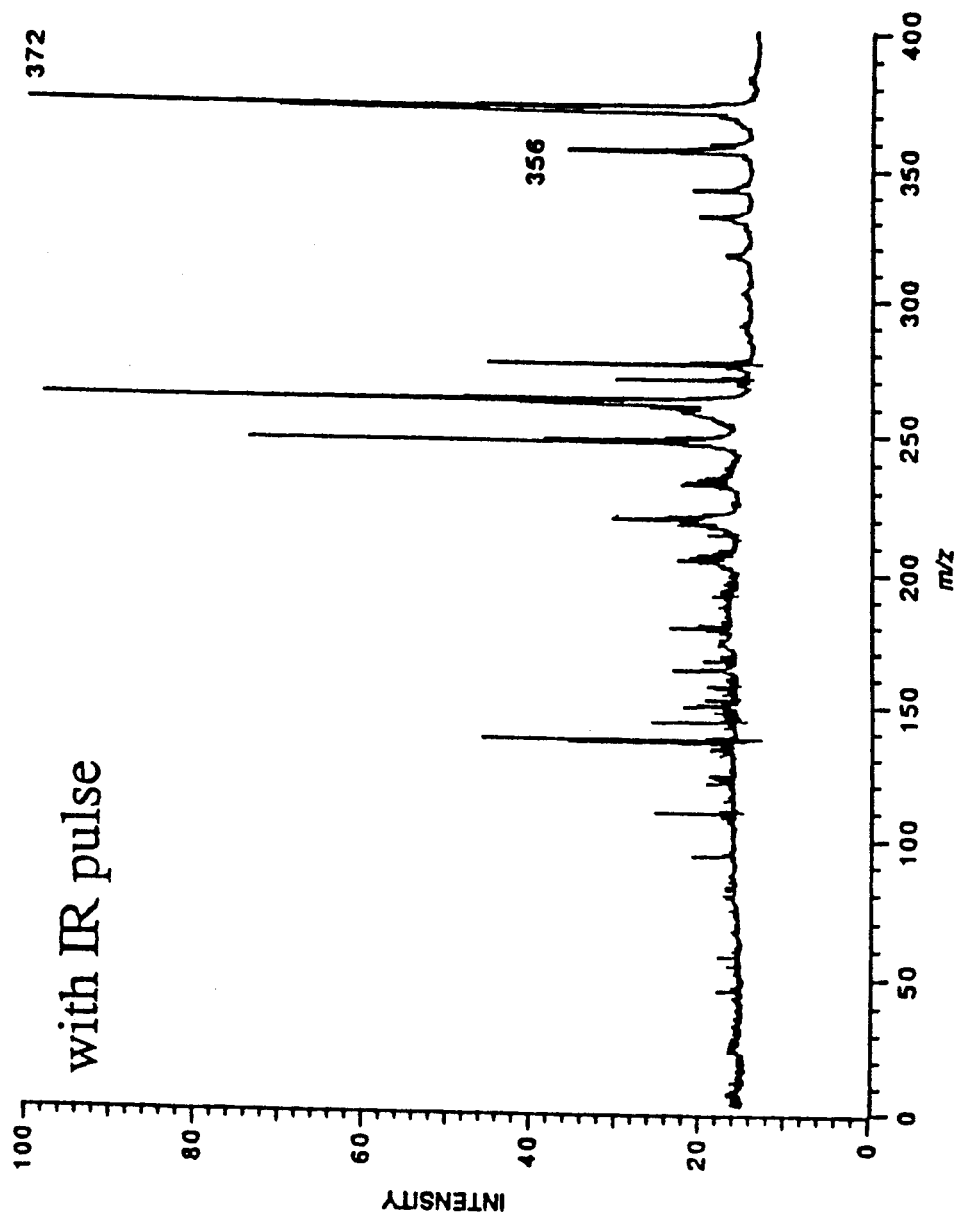
Fig. —3.

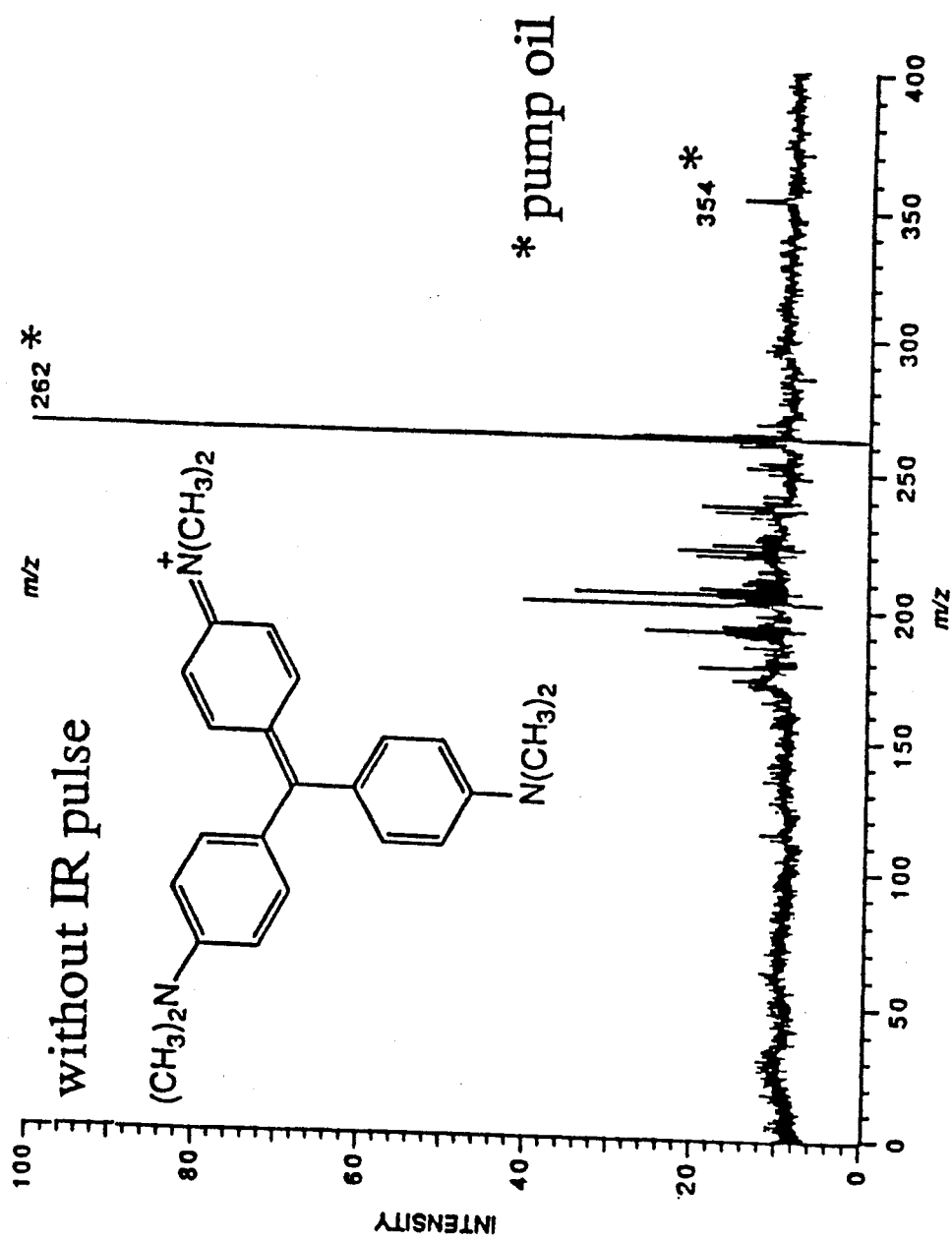
Fig. — 4.

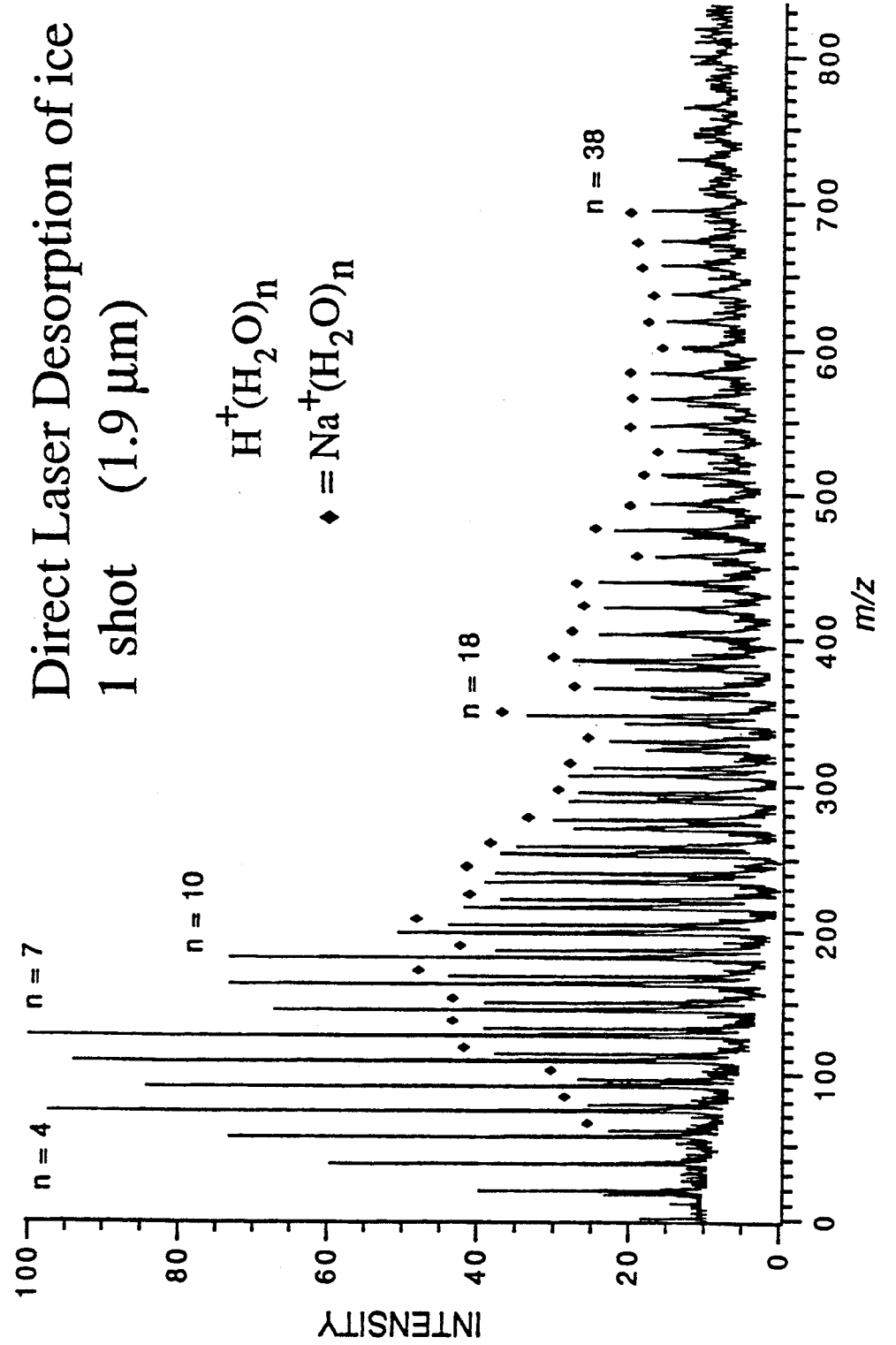
Fig. — 5.

METHOD AND APPARATUS FOR CONTINUOUS SAMPLE ICE MATRIX PRODUCTION FOR LASER DESORPTION IN MASS SPECTROMETRY

This invention was made with U.S. Government support under grant number CHE-8907477, awarded by the National Science Foundation. The government has certain rights to this invention.

FIELD OF THE INVENTION

The present invention relates generally to devices and methods for performing mass spectrometric analysis of material samples and, more specifically, to a technique of using ethylene glycol/water in the continuous production of a sample ice matrix for laser desorption in an ion source.

BACKGROUND OF THE INVENTION

Mass spectrometry is a widely accepted analytical technique for the accurate determination of molecular weights, the identification of chemical structures, the determination of the composition of mixtures and quantitative elemental analysis. It can accurately determine the molecular weights of organic molecules and determine the structure of the organic molecules based on the fragmentation pattern of the ions formed when the molecule is ionized.

Mass spectrometry relies on the production of ionized fragments from a material sample and subsequent quantification of the fragments based on mass and charge. Typically, positive, or negative ions are produced from the sample and accelerated to form an ion beam. Differing mass fractions within the beam are then selected using a mass analyzer, such as single-focusing or double-focusing magnetic mass analyzer, a time-of-flight mass analyzer, a quadrupole mass analyzer, or the like. A spectrum of fragments having different masses can then be produced, and the compound(s) within the material sample identified based on the spectrum.

Recent developments in matrix-assisted laser desorption make possible ionization of biomolecules in the 100,000 molecular weight range (Karas et al., *Biomed. Environ. Mass Spectrom.* 1989, 18, 841-843; Overberg et al., *Rapid Commun. Mass Spectrom.* 1990, 4, 293-296; Beavis et al., *Rapid Commun. Mass Spectrom.* 1989, 3, 233-237; and Nelson et al., *Rapid Commun. Mass Spectrom.* 1990, 4, 348-351). Sample molecules are mixed with a much higher proportion of relatively volatile matrix molecules. Vaporization of the matrix by the laser entrains the sample molecules into the gas phase. One matrix, frozen water (i.e., ice), has been successfully used for desorbing both proteins and nucleic acids into the gas phase (Nelson et al., *Rapid Commun. Mass Spectrom.* 1990, 4, 348-351). DNA molecules in the million molecular weight range have been vaporized intact with this technique (Nelson et al., *Science* 1989, 246, 1585-1587). In these experiments, solid samples are introduced into the vacuum chamber using a direct probe or other batch means. For example, Becker, U.S. Pat. No. 4,920,264, issued Apr. 24, 1990, describes a method for preparing non-volatile samples for mass analysis. In this process, certain organic solvents are first added to an aqueous sample solution before the solution is frozen to form a solid matrix. Thereafter, the matrix (approximately 1 μl in volume) is placed inside the vacuum chamber of a mass spectral analysis device where the matrix is subject to desorption and ionization. Prior to the desorption step, the matrix inside the chamber is cooled to a sufficiently low temperature to prevent it from evaporating. This preparation technique is rather cumbersome, in part, because the vacuum must be broken and reestablished for each successive sample.

In an attempt to combine liquid introduction with mass spectrometry, it has been demonstrated that water introduced into a vacuum chamber through a capillary can be made to produce ice at the capillary tip (Tsuda et al., *J. Chrom.* 1988, 456, 363-369). As water evaporates in the vacuum chamber, energy corresponding to the heat of vaporization is removed from the end of the capillary resulting in ice formation. Ice can be made to continuously flow from the capillary by applying localized heat near the tip. This is done by passing current through a resistive wire in contact with the capillary a few millimeters from the end. However, ice formation is irregular and difficult to control so that the desired continuous introduction is difficult to achieve. Typically, a block of ice forms at the end of the capillary which prevents further sample from entering the vacuum chamber. As a corollary, combining laser desorption and ionization with continuous sample introduction, for example to measure mass spectra of effluent from separation techniques (e.g., high performance liquid chromatography, gel permeation chromatography, or capillary electrophoresis) remains a problem.

SUMMARY OF THE INVENTION

It is an object of the present invention to provide a method for combining matrix-assisted laser desorption with continuous aqueous sample introduction for interfacing liquid sample to mass spectrometry.

It is another object of the invention to provide a method of mixing suitable solvents with water to enhance the spontaneous formation of ice matrix for laser desorption.

It is a further object of the present invention to provide a method of continuously introducing non-volatile biomolecules into the ion source of a mass spectrometer.

These and other objects are accomplished with the inventive mass spectrometer system that is based in part on the discovery that the addition of a suitable solvent, such as ethylene glycol, to an aqueous analyte solution substantially improves the reproducibility of ice formation at the end of a capillary that is inside a vacuum chamber so that a thread of ice is observed to exit the capillary. The inventive device comprises a vacuum chamber, a microcapillary with its outlet positioned inside the chamber, and means for adding suitable organic solvents to an aqueous sample solution of interest. Specifically, the invention can be used in time-of-flight mass spectrometry (TOF-MS) wherein direct capillary introduction is employed to continuously produce an ice matrix inside the vacuum chamber ion source from which ions are generated by laser desorption and photoionization.

As is apparent, the apparatus is readily adaptable for interfacing with a liquid chromatographic, electrokinetic, or other separation device so that effluent containing separated samples therefrom can be further analyzed in a mass spectrometer on a continuous basis. With the inventive device, it is unnecessary to interrupt the effluent flow, as is the case with conventional batch sample preparation techniques. Furthermore, the inventive technique can be automated to provide efficient identification of non-volatile compounds.

BRIEF DESCRIPTION OF THE DRAWING

FIG. 1 is a diagrammatic representation of a mass spectrometer with the inventive capillary electrophoresis - MS interface.

FIG. 2 is a diagrammatic representation of an ion source.

FIG. 3 is a mass spectrum of the dye molecule crystal violet.

FIG. 4 is a multi-photon ionization mass spectrum of gas phase background molecules.

FIG. 5 is a direct laser desorption spectrum of water clusters from ice.

DESCRIPTION OF THE PREFERRED EMBODIMENT

The present invention is based in part on the discovery that the addition of ethylene glycol into an aqueous matrix substantially improves the reproducibility of ice formation at the end of a tube which is positioned inside a vacuum chamber. This additive reduces the temperature at which ice forms. Other suitable solvents, including glycerol and benzyl alcohol, can also be used. Preferred solvents are low molecular weight 1-7 carbon organic solvents that are miscible with water and that are used at relatively low concentrations.

Appropriate solvents according to the invention can be added at any stage before the aqueous solution enters the vacuum chamber. For instance, in capillary zone electrophoresis, ethylene glycol can be added to the buffer so that effluent can be introduced continuously and directly into the ion source of a mass spectrometer. For other applications, the solvent can be dissolved in an aqueous solution stream just prior to entering the vacuum chamber. In either mode, good results are obtained when the solvent concentration is approximately 10% by volume. Generally, the solvent concentration should be from approximately 5 to 20% by volume. Adding the solvent has the concomitant effect of lowering the freezing point of the aqueous solution by approximately 5° to 20° C. When the appropriate solvent(s) is added, a thread of "ice" is observed to exit the column; however, without the solvent, crystalline ice forms which tends to plug the capillary outlet and prevent further flow of solution. With the present invention no internal heating inside the vacuum chamber is needed to promote continuous ice matrix formation.

Since with the invention, the solidified sample solution essentially "glides" through the capillary outlet and into the vacuum chamber, it follows that a liquid sample solution caused to flow continuously through the capillary can support and sustain the non-interrupted formation of successive solid matrices. (Successive matrices, rather than one long matrix, are formed since the initial thread of ice breaks off when it reaches a certain length.) The flow rate of the liquid sample solution is preferably less than or comparable to the rate at which the ice thread forms. Otherwise, some of the liquid sample solution would simply be injected into the chamber as a mist. The term "continuous" with regard to the inventive sample introduction technique thus refers to the non-interrupted formation of a solid sample matrix (or successive matrices) from a stream of liquid sample solution. As will be described below, molecules can be desorbed from the matrix and ionized for mass analysis.

A mass spectrometer system according to the invention is generally illustrated in FIG. 1 and includes an ion source 110, an ion optical system, that includes an einzel lens 130, steering plates 120, and ion deflection lens 121, positioned after the ion source to focus the parent ion beam 140 into the reflectron 150. In this embodiment, ions are generated in the ion source that contains ground electrode 113 and charged electrodes 111 and 112, by laser photoionization of an ice sample by desorption laser 114 and ionization laser 115. See Zare et al., U.S. Pat. No. 4,988,879, issued Jan. 29, 1991, incorporated herein by reference. Alternatively, the ions can be generated by direct laser desorption/ionization. The ion source is coupled through capillary 161 to a sample source 160 of the sample to be analyzed. The sample source could be, but is not limited to, effluent from electrophoretic or chromatographic separations. Appropriate means such as pumps and flow meters designated collectively as element 165 can be employed to regulate the flow rate of the sample going into the ion source 110. For instance, a syringe pump positioned at the atmospheric end of capillary 161 can be used to provide a continuous aqueous stream into the ion source. For capillary zone electrophoresis, an on-column frit could be used to define the potential at the end of the separation column. See Huang and Zare, Anal. Chem., 1990, 62, 443-446.

FIG. 2 illustrates the positioning of capillary 161 into ion source 110 with the tip of the 75 $\mu$m inner diameter capillary inserted approximately 1 mm inside the ion source between electrodes 111 and 112. When an aqueous solution is introduced into the capillary, the solution begins to solidify at a point in the capillary just before the outlet so that as aqueous solution continues to flow into the capillary, a thread of ice projects into the vacuum chamber. The thread is supported by the portion of ice that is inside the capillary tube. As ice, 162, exits the tip of the capillary, the first laser pulse vaporizes the ice and entrain sample molecules into the gas phase. Since the ice begins to form inside the capillary near the exit, a thread of ice forms if the tip of the ice is not exposed to laser radiation. The diameter of this ice thread corresponds roughly to the inner diameter of the capillary and can be made to extend over 15 mm into the vacuum. The time required for ice to traverse this dimension is approximately 3-6 seconds. In the event that ice is not vaporized, then some of the ice thread will be broken off by the force of its own weight. However, so long as liquid solution flows into the capillary, formation of ice matrix goes on uninterrupted. The size of the tube used is not critical, although preferably its inner diameter is about 500 $\mu$m or less; this is ultimately limited by the pumping speed of the vacuum system required to maintain a pressure in the ion source of approximately $10^{-5}$ torr or less. However, with the inventive method, ice can form at higher pressures (at least up to approximately $10^{-4}$ torr). When aqueous solution is initially introduced into the ion source through the capillary tube, the flow of the liquid is to some extent facilitated by the suction effect of the vacuum. However, it has been found that at approximately $10^{-5}$ torr operating pressure, the pressure differential does not adversely affect the continuous formation of ice matrix.

An embodiment of the present invention was built using a reflection time-of-flight mass spectrometer (R.M. Jordon Co.), modified to include an ion source for laser desorption and laser photoionization. The reflectron comprises grid decelerating electrodes 151 and 152 arranged at the inlet of the reflectron. The decelerating electrodes are positioned within the aperture of a series of diaphragm ring shaped reflectron lens (or mirrors) 153. Mounted in the aperture behind decelerating electrode 152 is reflector electrode 154. In the geometry employed, an ion of one particular mass, e.g., a parent ion, after being reflected is then accelerated along flight path 170 to microchannel plate detector 180. The present invention can also employ a reflectron time-of-flight mass spectrometer comprising a moveable, variable potential surface-induced dissociation surface. Such a device is described in Williams and Zare, U.S. patent application Ser. No. 07/739,904, filed Aug. 2, 1991, of common assignee.

FIG. 3 illustrates results of laser desorption from an ice matrix using the time-of-flight mass spectrometer as shown in FIG. 1 for the dye molecule crystal violet. The crystal violet was introduced (approximately 0.1 mg/ml) in a 50/50 solvent mixture of methyl alcohol/water at a rate of 2 $\mu$l/min. A double pulsed Nd-YAG laser was used to produce infrared (IR) photons at 1.0 $\mu$m (approximately 100 mJ) for desorption, and 266 nm photons (approximately 2 mJ) for ionization. The latter pulse is delayed by approximately 40 $\mu$s to allow the desorbed neutrals to leave the capillary, and move into the ionization region. Ions were subsequently accelerated with approximately 2 kV for time-of-flight mass analysis.

The resulting spectrum shows a large peak at m/z 372 corresponding to the molecular ion of this compound. Without the desorbing laser pulse, the mass spectrum measured (FIG. 4), shows no sample ions (ions present in this spectrum are due to multi-photon ionization of gas phase background molecules, primarily diffusion pump oil). Addition of ethylene glycol or glycerol improves the ice formation process without adversely affecting the laser desorption mass spectra.

Ions can also be produced directly from the ice matrix using a single laser pulse to both desorb and ionize. This is demonstrated with 1.9 $\mu$m photons (approximately 1 mJ) produced by Raman shifting 1.0 $\mu$m from a Nd-YAG laser in a hydrogen cell (68 cm length, 300 PSI of hydrogen). The results for pure water, introduced at 2 $\mu$l/min., are shown in FIG. 5. Water clusters, $(H_2O)_nH^+$, and Na containing water clusters, $(H_2O)_nNa^+$, are formed in abundance. Effects of additives on these mass spectra were not tested.

Although laser desorption/ionization is a preferred means of generating ions for mass spectral analysis, the ice can also be exposed to other sources of energy including microwave radiation, ion beam bombardment, electron beam bombardment, and fast atom bombardment.

It is to be understood that while the invention has been described above in conjunction with preferred specific embodiments, the description and examples are intended to illustrate and not limit the scope of the invention, which is defined by the scope of the appended claims.

It is claimed:

1. A continuous sample introduction method for mass spectral analysis comprising the steps of:
   providing an aqueous solution of sample molecules to be analyzed,
   adding to said aqueous solution one or more solvents that lowers the freezing temperature of said aqueous solution by approximately 5° to 20° C.; and
   introducing said aqueous solution into a vacuum chamber through a conduit having an outlet positioned inside said vacuum chamber, wherein said aqueous solution is introduced through said conduit outlet at such a flow rate as to enable said aqueous solution to solidify to form a thread of solid matrix.

2. The continuous sample introduction method as defined in claim 1, said conduit comprising a capillary with an inner diameter of about 500 $\mu$m or less, wherein the step of adding solvents comprises adding one or more low molecular weight organic compounds to said aqueous solution so that the organic solvents comprise approximately 5 to 20% by volume of said aqueous solution that enters the capillary.

3. The continuous sample introduction method as defined in claim 2 wherein the introduction step causes the formation of a thread of solid matrix having a diameter of approximately 500 $\mu$m or less.

4. The continuous sample introduction method as defined in claim 3 wherein said method further comprises the step of exposing a portion of said thread of solid matrix to a source of energy.

5. The continuous sample introduction method as defined in claim 2 wherein the step of adding solvents comprises adding one or more organic compounds selected from the group consisting of ethylene glycol, glycerol, and benzyl alcohol.

6. The continuous sample introduction method as defined in claim 2 wherein the step of adding solvents comprises adding ethylene glycol so that the ethylene glycol comprises approximately 10% by volume of said aqueous solution.

7. The continuous sample introduction method as defined in claim 2 wherein the step of introducing aqueous solution comprises maintaining the aqueous solution flow into the capillary at a rate which is less than or comparable to the rate at which said aqueous solution solidifies.

8. The continuous sample introduction method as defined in claim 4 wherein the step of exposing a portion of the solid matrix to a source of energy causes sample molecules to be desorbed from said portion of solid matrix to form gaseous sample molecules.

9. The continuous sample introduction method as defined in claim 8 further comprising the step of:
   exposing said gaseous sample molecules to an ionization source of sufficient intensity to ionize said gaseous sample molecules.

10. The continuous sample introduction method as defined in claim 4 wherein the step of exposing a portion of said thread of solid matrix to a source of energy comprises directing a first pulse of laser radiation to vaporize a portion of said solid matrix into gaseous sample molecules.

11. The continuous sample introduction method as defined in claim 10 further comprising the step of:
    exposing said gaseous sample molecules to a second pulse of laser radiation to photoionize said gaseous sample molecules into ions.

12. The continuous sample introduction method as defined in claim 11 wherein the steps of vaporizing a portion of said solid matrix and of photoionizing said gaseous sample molecules are carried out in sequential cycles.

13. The continuous sample introduction method as defined in claim 12 wherein said vacuum chamber is located in an ion source of a mass spectrometer, said method further comprising the step of focusing said ions into a mass spectral analysis zone.

14. The continuous sample introduction method as defined in claim 4 wherein the step of exposing a portion of said solid matrix to a source of energy comprises applying successive pulses of laser radiation in order to vaporize successive portions of said thread of solid matrix that enters said vacuum chamber.

15. The continuous sample introduction method as defined in claim 4 wherein the step of exposing a portion of said thread of solid matrix to a source of energy comprises directing a pulse of laser radiation to desorb and ionize sample molecules from said matrix.

16. The continuous sample introduction method as defined in claim 15 wherein said vacuum chamber is located in an ion source of a mass spectrometer and further comprising the step of focusing sample ions into a mass spectral analysis zone.

17. An apparatus for continuously forming a thread of solid sample matrix comprising:
a vacuum chamber;
conduit means for introducing said aqueous solution into said vacuum chamber, wherein said conduit means has an outlet positioned inside said vacuum chamber; and
means for continuously providing an aqueous solution of sample, said solution containing one or more organic solvents that lowers the freezing point of said aqueous solution by approximately 5° to 20° C. wherein said providing means is in fluid communication with said conduit means so that said solution is introduced into said vacuum chamber at such a flow rate as to enable said solution to solidify into a thread of solid matrix.

18. The apparatus for continuously forming solid sample matrix as defined in claim 17 wherein said conduit comprises a capillary having an inner diameter of approximately 500 μm or less.

19. The apparatus for continuously forming solid sample matrix as defined in claim 17 further comprising means for regulating the flow of aqueous solution into the capillary so that the flow rate is less than or comparable to the rate at which said aqueous solution solidifies.

20. The apparatus for continuously forming solid sample matrix as defined in claim 18 wherein said organic solvents comprise low molecular weight organic compounds comprising approximately 5 to 20% by volume of said aqueous solution.

21. The apparatus for continuously forming solid sample matrix as defined in claim 20 wherein said solvents comprise one or more organic compounds selected from the group consisting of ethylene glycol, glycerol, and benzyl alcohol.

22. The apparatus for continuously forming solid sample matrix as defined in claim 18 wherein said solvents comprise ethylene glycol so that the ethylene glycol comprises approximately 10% by volume of said aqueous solution.

23. The apparatus for continuously forming solid sample matrix as defined in claim 18 further comprising means for desorbing sample molecule from said solid matrix to form gaseous sample molecules.

24. The apparatus for continuously forming solid sample matrix as defined in claim 23 further comprising means for ionizing said gaseous sample molecules.

25. The apparatus for continuously forming solid sample matrix as defined in claim 24 wherein the desorption means comprises a first laser from which a first pulse of laser radiation is directed at a portion of the solid matrix and wherein the ionization means comprises a second laser from which a second pulse of laser radiation is directed at said gaseous sample molecule.

26. The apparatus for continuously forming solid sample matrix as defined in claim 25 further comprising means for generating said first pulse of laser radiation and said second pulse of laser radiation in sequential cycles.

27. The apparatus for continuously forming solid sample matrix as defined in claim 25 wherein the vacuum chamber is located in an ion source of a mass spectrometer.

28. The apparatus for continuously forming solid sample matrix as defined in claim 18 further comprising means for directly ionizing sample molecules in said matrix into gaseous sample ions.

29. The apparatus for continuously forming solid sample matrix as defined in claim 28 wherein said ionization means comprises a laser.

30. The apparatus for continuously forming solid sample matrix as defined in claim 29 wherein the vacuum chamber is located in an ion source of a mass spectrometer.

* * * * *